(12) United States Patent
Gagnon

(10) Patent No.: US 10,023,609 B2
(45) Date of Patent: Jul. 17, 2018

(54) METHODS FOR REDUCING CHROMATIN CONTENT IN PROTEIN PREPARATIONS BY TREATMENT WITH ALKYL CATIONS

(71) Applicant: AGENCY FOR SCIENCE, TECHNOLOGY AND RESEARCH, Singapore (SG)

(72) Inventor: Peter Stanley Gagnon, Singapore (SG)

(73) Assignee: AGENCY FOR SCIENCE, RESEARCH AND TECHNOLOGY, Singapore (SG)

(*) Notice: Subject to any disclaimer, the term of this patent is extended or adjusted under 35 U.S.C. 154(b) by 0 days.

(21) Appl. No.: 15/121,686

(22) PCT Filed: Feb. 27, 2014

(86) PCT No.: PCT/SG2014/000087
§ 371 (c)(1),
(2) Date: Aug. 25, 2016

(87) PCT Pub. No.: WO2015/130223
PCT Pub. Date: Sep. 3, 2015

(65) Prior Publication Data
US 2016/0362448 A1     Dec. 15, 2016

(51) Int. Cl.
| | | |
|---|---|---|
| *C07K 1/32* | (2006.01) | |
| *B01D 15/26* | (2006.01) | |
| *C07K 1/14* | (2006.01) | |
| *C07K 1/36* | (2006.01) | |
| *C07K 16/00* | (2006.01) | |
| *B01D 15/32* | (2006.01) | |
| *B01D 15/36* | (2006.01) | |
| *B01D 15/38* | (2006.01) | |

(52) U.S. Cl.
CPC .............. *C07K 1/32* (2013.01); *B01D 15/265* (2013.01); *C07K 1/145* (2013.01); *C07K 1/36* (2013.01); *C07K 16/00* (2013.01); *B01D 15/327* (2013.01); *B01D 15/361* (2013.01); *B01D 15/3828* (2013.01)

(58) Field of Classification Search
CPC ....................................................... C07K 1/32
See application file for complete search history.

(56) References Cited

U.S. PATENT DOCUMENTS

| | | | |
|---|---|---|---|
| 4,797,474 A | | 1/1989 | Patroni et al. |
| 2012/0142033 A1* | | 6/2012 | Fujiwara ............ B01D 11/0288 435/7.92 |

FOREIGN PATENT DOCUMENTS

| | | | |
|---|---|---|---|
| JP | 2003-128699 | * | 5/2003 |
| WO | 2013180647 A1 | | 12/2013 |
| WO | 2014133456 A1 | | 9/2014 |

OTHER PUBLICATIONS

Gan et al., "Characterization and removal of aggregates formed by nonspecific interaction of IgM monoclonal antibodies with chromatin catabolites during cell culture production", Journal of Chromatography A 1291, (2013), pp. 33-40.
Hamada, et al., "Effect of Additives on Protein Aggregation," Current Pharmaceutical Biotechnology, Bentham Science Publishers, NL, vol. 10, No. 4, Jun. 1, 2009, pp. 400-407.
Andersson, et al., "Protein stabilizing effect of polyethyleneimine," Journal of Biotechnology, Elsevier, Amsterdam, NL, vol. 72, No. 1-2, Jun. 11, 1999, pp. 21-31.
Extended European Search Report dated Sep. 4, 2017, from related EP Application No. EP14883801.

\* cited by examiner

*Primary Examiner* — Suzanne M Noakes
(74) *Attorney, Agent, or Firm* — Pillsbury Winthrop Shaw Pittman LLP

(57) ABSTRACT

A method of reducing aggregate content in a preparation having a target protein includes contacting the preparation with an alkyl cation to form a mixture, and contacting the mixture with at least one functionalized solid to remove excess alkyl cation.

17 Claims, No Drawings

METHODS FOR REDUCING CHROMATIN CONTENT IN PROTEIN PREPARATIONS BY TREATMENT WITH ALKYL CATIONS

RELATED APPLICATIONS

This application is a U.S. National Stage of International Patent Application No. PCT/SG2014/000087, filed Feb. 27, 2014, entitled METHODS FOR REDUCING CHOMATIN CONTENT IN PROTEIN PREPARATIONS BY TREATMENT WITH ALKYL CATIONS, and naming inventor Peter Stanley Gagnon, which published as International Patent Publication No. WO/2015/130223 on Sep. 3, 2015. The entire content of the forgoing application is incorporated herein by reference, including all text, tables and drawings.

BACKGROUND

Embodiments disclosed herein relate to methods for enhancing purification of proteins, including antibodies. They particularly relate to methods for reducing the level of aggregates and can be combined with methods of cell culture harvest clarification. They further relate to integration of these capabilities with other purification methods to achieve a desired level of protein purity.

Aggregate removal is an important aspect of protein purification. It has been shown that low concentrations of the yellow fluorescent heterocyclic dye ethacridine reduces aggregate content of antibody preparations, and that this result may be due, in part, to chromatin removal (Gan et al J. Chromatography A 1291 (2013) 33-40). Ethacridine has a long history as a protein precipitating agent.

The surfactant cetrimonium bromide is used as a topical antiseptic. It is also used in the production of gold nanoparticles, and widely in hair-care products. It is used in the field of protein analysis where it improves resolution of complex glycoproteins in polyacrylamide gel electrophoresis, and in DNA extraction. It is not known to have applications in the field of protein fractionation.

SUMMARY

A method of reducing aggregate content in a preparation comprising a target protein, the method comprising contacting the preparation with an alkyl cation to form a mixture and contacting the mixture with at least one functionalized solid to remove excess alkyl cation.

DETAILED DESCRIPTION OF THE DISCLOSED METHODS

The methods disclosed herein provide a means of reducing protein aggregates in a sample containing a desired protein by treating the sample with alkyl cations. In some embodiments, the reduction of complexes and/or aggregates may be achieved with ultralow levels of alkyl cations. In some embodiments, the sample may be treated at elevated conductivity values (using elevated salt concentration). In some embodiments, the treated sample may be subsequently exposed to solid materials bearing chemical moieties that selectively remove alkyl cations and aggregates from the protein preparation.

Additionally, kits are provided for the purification of proteins by the methods disclosed herein. In some embodiments the disclosed methods provides for the reduction of aggregates from preparations of antibodies or other proteins through the contact of such desired protein with one or more alkyl cation. In some embodiments, the disclosed methods may be practiced at a range of conductivity levels from so-called physiological conditions to conductivity values up to three or more times greater than such conditions. Such elevated conductivity levels may permit the method to be applied to acidic proteins without risking their precipitation during treatment, and thereby increase the diversity of desired protein species to which the disclosed methods may be applied. As a point of reference, physiological conductivity is generally understood to include a range from about 12 milliSiemens per cm (mS/cm) to about 17 mS/cm.

In some embodiments, the disclosed methods may be practiced with ultralow concentrations of the alkyl cations; such as about 0.01% to about 0.05%, including any values and ranges in between. In some embodiments, the disclosed methods provide contacting the treated protein preparation with solid materials that enhance the overall ability of the treatment to reduce aggregate content, usually in parallel with reducing host protein contamination, and provide the additional advantage of removing excess alkyl cations. In some embodiments, the alkyl cation is cetyl trimethyl ammonium bromide.

In some embodiments, the disclosed methods provide for reducing levels of aggregates which have high molecular weight in comparison with the desired protein, such as homo-aggregates, and also for reducing levels of aggregates of hydrodynamic size only modestly greater than the desired protein, such as hetero-aggregates. In some embodiments, aggregates comprise hetero-aggregates of the desired protein and a contaminant and in certain such embodiments the contaminant is a nucleic acid, nucleotide, endotoxin, metal ion, protein, lipid, or cell culture media component. In some embodiments, the presence of homo-aggregates of the desired protein is substantially eliminated. In some embodiments, the presence of hetero-aggregates of the desired protein and a contaminant is substantially eliminated. In some embodiments, the presence of homo- and hetero-aggregates including the desired protein are substantially eliminated.

In some embodiments, the disclosed methods additionally provide for the reduction of contaminants such as DNA, endotoxin, and virus levels along with reduction of aggregates. In some embodiments the disclosed methods are practiced with the additional inclusion of antiviral agents beyond the alkyl cation itself.

In some embodiments, the protein species of interest (e.g., the desired protein to be purified) is of recombinant origin, and the protein preparation may include a cell-containing cell culture harvest, a cell culture supernatant, clarified cell culture supernatant, an eluate from a chromatography column, or protein-containing solution obtained from a previous stage of purification. In some embodiments, the protein preparation contains an antibody and in certain of such embodiments the antibody is an IgG, an IgM, or a fragmentary form thereof, or a fusion protein of an antibody or antibody fragment, such as an Fc-fusion protein. In some embodiments, the desired protein may be a clotting protein, such as Factor VIII. In some embodiments, the desired protein may be a peptide hormone, such as human growth hormone.

In some embodiments, the disclosed methods are practiced such that the conductivity of the sample is at a sufficiently high level to substantially avoid precipitation of the desired protein from the sample. Conductivity may be adjusted by addition of salts or diluents according to methods known in the art. In some embodiments, the conductivity is 5 mS/cm, 10 mS/cm, 15 mS/cm or 20 mS/cm greater than the level determined to be needed to avoid substantial precipitation of the desired protein. In some embodiments, the conductivity is greater than 20 mS/cm, 25 mS/cm, 30 mS/cm, 35 mS/cm, 40 mS/cm, 45 ms/cm or greater than 45 mS/cm. The ability of the method to remove important subsets of contaminants at elevated conductivities represents one of the surprising features of the disclosed methods, since charge interactions in these system are known to be reduced at elevated conductivities. At conductivities of 25 mS/cm and higher for example, only a minority of negatively charged proteins are known to bind to electropositive surfaces. Apart from the present method, application of most electropositive agents to preparations of IgG antibodies occurs at conductivities less than 5 mS/cm, and usually with the additional operating requirement of alkaline pH. Such an operating pH is not a requirement of the present method. It will be apparent to the person of ordinary skill in the art that elevated conductivity may have the effect of weakening internal electrostatic associations within aggregates and thereby increase the ability of the method to achieve dissociation of aggregates and/or removal of contaminants associated with the desired protein.

In some embodiments, the alkyl cation is cetyl trimethyl ammonium bromide (IUPAC name: N,N,N-Trimethyl-1-hexadecanammonium bromide, an analogue, or a salt thereof. Cetyl trimethyl ammonium bromide is also known as cetrimonium bromide. Analogs include alkyl cations with different numbers of carbon residues, such as 12, 13, 14, 15, 16, 17, 18, 19, 20, 21, 22, 23, or 24 carbons which may be in a branched or linear configuration. The cationic group may consist of a quaternary amine, a primary amine, a secondary amine, a tertiary amine, or a combination of positive charges such as embodied by Tris(2-aminoethyl) amine.

In some embodiments, the alkyl cation is provided at substantially the lowest concentration sufficient to promote the desired degree of reduction of aggregates. In some embodiments, the concentration of the alkyl cation may be less than (on a weight per volume basis) 1%, 0.5%, 0.25%, 0.1%, 0.05%, 0.04%, 0.025%, or 0.001%. In some embodiments the electropositive organic additive is provided in concentrations of 0.01-0.04% or 0.02-0.025%.

In some embodiments, the disclosed methods may be practiced at pH levels chosen to avoid or limit precipitation of the desired protein while reducing the amount of aggregates in the sample. The pH level may be adjusted by conventional means and may be chosen in conjunction with the selection of the conductivity. In some embodiments, the pH of the sample is between approximately 4 and approximately 9, between approximately 5 and approximately 8, or between approximately 6 and approximately 7.5.

In some embodiments, the sample is additionally contacted with an antiviral agent beyond the alkyl cation iteself. In certain of such embodiments, the antiviral agent is a non-multivalent organic cation, such as a benzalkonium chloride, chlorhexidine, ethacridine, or tri (n-butyl) phosphate. Such antiviral agents may be present in an amount less than approximately 1% (w/v), less than approximately 0.1% (w/v), or less than approximately 0.01% (w/v) or less than approximately 0.001%.

In some embodiments, the method additionally includes the step of contacting the sample with a ureide in an amount sufficient for the ureide to be undissolved in the sample. The supernatant containing the desired protein can then be separated from the balance of the sample including precipitated contaminants. In certain of such embodiments the ureide is supplied prior to the step of contacting the sample with the electropositive organic additive, in others the ureide is supplied substantially simultaneously with the step of contacting the sample with the electropositive organic additive, and in yet others the ureide is supplied after the step of contacting the sample with the electropositive organic additive. In certain such embodiments, the ureide can be any of uric acid, hydantoin (imidazolidine-2,4-dione), alcloxa, aldioxa, hemocane, ureidohydantoin, 5-ureidohydantoin, glyoxylureide, glyoxylic acid diureide, 2,5-dioxo-4-imidazolidinyl urea (allantoin), imidazolydinyl urea, diimidazolydinyl urea, and a purine. In some embodiments the ureide is allantoin and in some such cases the allantoin is present in concentrations greater than 0.56% (w/v), 1%, 1.5%, 2%, or greater. In some embodiments the ureide is uric acid and in some such cases the uric acid is present in concentrations greater than 0.0025% (w/v), 0.005%, 0.01%, 0.05%, 0.1%, 1% or greater.

In some embodiments, the method additionally includes the step of contacting the sample with a ureide in an amount where the ureide is fully dissolved. In certain such embodiments, the soluble ureide can be urea, imidazolydinal urea, or another ureide. In some embodiments the ureide is urea and in some such cases the urea is present in concentrations greater than 0.5 M, or greater than 1 M, or greater than 2 M, or greater than 4 M, or than 6 M, or greater than 8 M. This emphasizes again the surprising nature of the method, where avoidance of precipitation is a particular object of the method. Highly soluble ureides such as urea have the general effect of increasing the solubility of many compounds, which is to say their presence opposes the formation of precipitates.

In some embodiments, the utility of the disclosed methods is enhanced by the fact that they also accelerate sedimentation of cell debris in cell culture harvests, and substantially reduces levels of DNA, endotoxin, and virus, when present. Experimental data suggest that the ability of some ureides to preferentially interact with aggregates, endotoxin, and virus contribute to these results, and that low levels of dissolved ureides may contribute to the higher antibody recovery they support in comparison to treatment with multivalent cations in the absence of ureides. Following treatment, solid materials may be removed by sedimentation or filtration, leaving the substantially aggregate-free protein in the supernatant.

In some embodiments, the disclosed methods may be practiced with the additional step of contacting the sample with a soluble organic modulator such as a nonionic organic polymer, organic solvent, surfactant, or ureide. In certain of such embodiments the step of contacting the sample with the organic modulator occurs prior to the step of contacting the sample with the electropositive organic additive. In others, the step of contacting the sample with the organic modulator occurs substantially simultaneously with the step of contacting the sample with the electropositive organic additive. In yet others, the step of contacting the sample with the organic modulator occurs after the step of contacting the sample with the electropositive organic additive. In some embodiments, the organic modulator is a nonionic organic polymer such as polyethylene glycol, polypropylene glycol and polybutylene glycol and in certain of such embodiments the nonionic organic polymer has an average molecular weight of approximately 1000D or less, 500 D or less, 250 D or less, or 100 D or less. In some embodiments, the organic modulator is an organic solvent such as ethylene glycol, propylene glycol, butylene glycol, dimethylsulfoxide, ethanol, or phenoxyethanol. In some embodiments, the organic modulator is provided at a concentration of approximately 1% (w/v) or greater. In some embodiments, the organic modulator is a surfactant such as Tween, triton, CHAPS, CHAPSO or octyl glucoside and in certain of such embodiments the surfactant is provided at a concentration of approximately 1% (w/v) or less, approximately 0.1% or less or approximately 0.02% (w/v) or less. In some embodiments, the organic modulator is a ureide provided in a subsaturating amount and in certain of such embodiments the ureide is urea, hydantoin, or allantoin.

In some embodiments, the disclosed methods provide for a kit for the convenient practice of certain methods of the disclosed methods. Such kit may provide reagents useful for the practice of the disclosed methods such one or more of multivalent organic cations, ureides, organic modulators, antiviral agents, and reagents for the adjustment of conductivity. The kit may provide materials in amounts and concentrations adapted to the practice of the disclosed methods for use in the purification of proteins. Such kits may be adapted for use with certain proteins such as IgG or IgM antibodies and may be adapted to quantities suitable for certain scales of protein preparation and purification.

In some embodiments, the disclosed methods may be followed by contact of the sample with solid materials with the intent of the solids having the effect of selectively removing the excess alkyl cations or other sample components from the sample prior to additional processing.

In some embodiments, the disclosed methods may be combined with conventional protein purification methods to achieve higher levels of purification or to remove other contaminants. For example, the disclosed methods may be practiced in preparation for conventional purification methods involving precipitation, chromatography, and liquid-liquid extraction methods. It is within the ability of a person of ordinary skill in the art to develop appropriate conditions for these methods and integrate them with the disclosed methods described herein to achieve the desired purification of a product.

In some embodiments, operating conditions may be varied with respect to pH, and/or by the presence of chelating agents, organic polymers or solvents, surfactants, chaotropes, and various species of salts in order to modulate the degree to which aggregates are reduced and the desired protein remains in solution.

In some embodiments, there are provided methods of reducing aggregate content in a preparation comprising a target protein, the method comprising contacting the preparation with an alkyl cation to form a mixture and contacting the mixture with at least one functionalized solid to remove excess alkyl cation.

In some embodiments, methods may further comprise contacting the mixture with an aryl cation. In some such embodiments, the aryl cation may be ethacridine or methylene blue. In some embodiments, the combined concentration of the alkyl and aryl cations may be the same as the concentration as when the alkyl cation is used alone. In such embodiments, the alkyl cation is present in a non-zero amount.

In some embodiments, methods disclosed herein may further comprise contacting the mixture, simultaneously or sequentially, with at least one electropositive solid to further reduce aggregate content of the preparation.

In some embodiments, the alkyl cation comprises a bromide or chloride salt of a quaternary ammonium cation selected from the group consisting of cetrimonium, cetyl trimethyl ammonium, N,N,N-Trimethyl-1-hexadecanammonium, N,N,N-Trimenthyl-1-heptadecanammonium, N,N, N-Trimethyl-1-octadecanarnmonium, N,N,N-Trimethyl-1-pentadecanammoniurn, and N,N,N-Trimethyl-1-tetradecanammonium.

In some embodiments, the alkyl cation is present in a concentration range selected from the group consisting of: (a) from about 0.001% to about 1%; (b) from about 0.01 to about 1%, and (c) from about 0.02 to about 0.03%.

In some embodiments, allantoin is present in a concentration range selected from the group consisting of (a) from about 0.6 to about 50%; (b) from about 1 to about 10%; and (c) from about 1 to about 2%.

In some embodiments an operating conductivity is within a range selected from the group consisting of: (a) from about 0.1 to about 50 mS/cm; (b) from about 1 to about 30 mS/cm; and (c) from about 5 to about 15 mS/cm.

In some embodiments, an operating pH is in a range selected from the group consisting of: (a) from about 4 to about 10; (b) from about 5 to about 9; and from about 6 to about 8.

In some embodiments, the mixture further comprises an antiviral agent that is not the alkyl cation, the antiviral agent being selected from the group consisting of chlorhexidine, benzalkonium chloride, methylene blue, ethacridine, and tri (n-butyl) phosphate.

In some embodiments, a surface of the at least one functionalized solid promotes a chemical interaction selected from the group consisting of: electrostatic interactions, hydrophobic interactions, hydrogen bonding, and metal affinity.

In some embodiments, the at least one functionalized solid is particulate.

In some embodiments, the target protein comprises one selected from the group consisting of a recombinant protein, an antibody, a growth hormone, and a clotting factor.

In some embodiments, the protein preparation is one selected from the group consisting of a cell-containing cell culture harvest, a substantially cell-free cell culture harvest, and a partially purified protein.

In some embodiments, there are provided kits for the convenient practice of the method disclosed herein. Such kits may include all the necessary reagent for carrying out the methods along with instructions.

The following terms are defined so that the disclosed methods may be understood more readily. Additional definitions are set forth throughout the detailed description.

"Aggregate(s)" refers to an association of two or more molecules that is stable at physiological conditions and may remain stable over a wide range of pH and conductivity conditions. Aggregates frequently comprise at least one biomolecule such as a protein, nucleic acid, or lipid and another molecule or metal ion. The association may occur through any type or any combination of chemical interactions. Aggregates of antibodies can be classified into two categories: "Homoaggregates" refers to a stable association of two or more proteins of identical composition; "Heteroaggregates" refers to a stable association of one or more proteins of identical or different composition, optionally associated with one or more non-protein molecules. The non-protein component may consist of one more entities from the group consisting of a nucleotide, an endotoxin, a metal ion, a lipid, or a cell culture media component.

"Antibody" refers to an immunoglobulin, composite, or fragmentary form thereof The term may include but is not limited to polyclonal or monoclonal antibodies of the classes IgA, IgD, IgE, IgG, and IgM, derived from human or other mammalian cell lines, including natural or genetically modified forms such as humanized, human, single-chain, chimeric, synthetic, recombinant, hybrid, mutated, grafted, and in vitro generated antibodies. "Antibody" may also include composite forms including but not limited to fusion proteins containing an immunoglobulin moiety. "Antibody" may also include antibody fragments such as Fab, F(ab')$_2$, Fv, scFv, Fd, dAb, Fc and other compositions, whether or not they retain antigen-binding function.

"Endotoxin" refers to a toxic heat-stable lipopolysaccharide substance present in the outer membrane of gram-negative bacteria that is released from the cell upon lysis.

"Non-ionic organic polymer" refers to a naturally occurring or synthetic hydrocarbon composed of linked repeating organic subunits that lack charged groups. It may be linear, dominantly linear with some branching, or dominantly branched. Examples suitable to practice the disclosed methods include but are not limited to polyethylene glycol (PEG), polypropylene glycol, and polyvinylpyrrolidone (PVP). PEG has a structural formula HO—(CH$_2$—CH$_2$—O)$_n$—H. Examples include, but are not limited to compositions with an average polymer molecular weight ranging from less than 100 to more than 1000 daltons.

"Alkyl cation" refers to an organic cation consisting of 12 or more carbon atoms in a continuous straight or branched configuration, bearing at least one positive charge where the positive charge which may include additional carbon atons. One example is cetyl trimethyl ammonium bromide. Alkyl cations may be used as salts, including bromides, chlorides, and stearates, among others.

"Aryl cation" refers to an organic cation consisting of 3 rings in a coplanar arrangement, bearing at least one positive charge that may be expressed through a nitrogen atom or a sulfur atom. Examples include ethacridine (7-ethoxyacridine-3,9-diamine; 2-hydroxypropanoic acid) and methylene blue (7-(dimethylamino)phenothiazin-3-ylidene]-dimethylazanium), as well as analogs, derivatives, and salts thereof.

"Organic solvent" refers to naturally occurring or synthetic organic compound existing in a liquid state. Examples suitable to practice the disclosed methods include but are not limited to ethylene glycol, propylene glycol, dimethyl sulfoxide, ethanol, and phenoxyethanol.

"Organic polymer" refers to a naturally occuring synthetic polymer of an organic monomer. Examples include but are not limited to polyethylene glycol, polypropylene glycol, dextran, or cellulose, among others.

"Polynucleotide" refers to a biopolymer composed of multiple nucleotide monomers covalently bonded in a chain. DNA (deoxyribonucleic acid) and RNA (ribonucleic acid) are examples of polynucleotides.

"Protein" refers to any of a group of complex organic macromolecules that contain carbon, hydrogen, oxygen, nitrogen, and usually sulfur and are composed principally of one or more chains of amino acids linked by peptide bounds. The protein may be of natural or recombinant origin. Proteins may be modified with non-amino acid moieties such as through glycosylation, pegylation, or conjugation with other chemical moieties. Examples of proteins include but are not limited to antibodies, clotting factors, enzymes, and peptide hormones.

"Undissolved ureide" refers to a solution containing an amount of ureide in excess of its maximum solubility under the conditions prevailing in a particular protein preparation. In some embodiments, the disclosed methods provides a sample with a ureide present in an amount greater than such ureide's solubility in such sample under the conditions for such sample such that some fraction of such ureides is present in an undissolved form in the sample.

"Surfactant" includes "surface active agents" such as a class of organic molecules that generally embody a hydrophobic portion and a hydrophilic portion, causing them to be referred to as amphiphilic. At sufficient concentrations in aqueous solutions, surfactants can self-associate into clusters with the hydrophobic portions concentrated at the center to minimize contact with water, and the hydrophilic portions radiating outwards to maximize contract with water. In the presence of biological preparations, especially those containing materials that have a hydrophobic character or possess areas of hydrophobic character, the hydrophobic portion of surfactants tend to associate spontaneously with some portions of the hydrophobic material and increase their solubility through the influence of the hydrophilic portion of the surfactant. They may also be used to modulate hydrophobic interactions that occur between differing hydrophobic materials both dissolved in an aqueous solvent. Examples of surfactants suitable for practicing some embodiments of the disclosed methods include but are not limited to nonionic surfactants such as polysorbate surfactants (e.g., Tween 20, Polyoxyethylene (20) sorbitan monolaurate, and Tween 80, Polyoxyethylene (20) sorbitan monooleate) and Triton (e.g., polyethylene glycol p-(1,1,3,3-tetramethylbutyl)-phenyl ether), and zwitterionic surfactants such as CHAPS (3-[(3-Cholamidopropyl)dimethylammonio]-1-propanesulfonate), CHAPSO (3-[(3-cholamidopropyl) dimethylammonio]-2-hydroxy-1-propanesulfonate), and octyl glucoside (e.g., (2R,3S,4S,5R,6R)-2-(hydroxymethyl)-6-octoxyoxane-3,4,5-triol).

"Virus" or "virion" refers to an ultramicroscopic (roughly 20 to 300 nm in diameter), metabolically inert, infectious agent that replicates only within the cells of living hosts, mainly bacteria, plants, and animals: composed of an RNA or DNA core, a protein coat, and, in more complex types, a surrounding envelope.

In preparation for using the disclosed methods according to some embodiments, it will be necessary to select a alkyl cation. Experimental data reveal cetyl trimethyl ammonium bromide to be desirable for its effectivity in reducing aggregates, in addition its ability to inactivate virus. Its use as an anti-malarial drug and therapeutic agent for treatment of methemoglobinenia highlights its compatibility with in vivo human use, and it is listed in the U.S. Pharmacopeia.

In the course of evaluation of alkyl cations for use in some embodiments, the conditions for application may be investigated as follows. The use of alkyl cations potentially imposes some restrictions on the conditions that may be used to practice the method in some embodiments. For example, it can be desirable to employ conditions that substantially prevent strong interactions between the alkyl cations and the protein of interest. A simple method to obtain an approximation of such conditions is to apply the protein of interest to an anion exchanger and elute it in a salt gradient. A salt concentration just above the threshold at which the protein elutes roughly identifies the minimum conductivity at which the method may be most effectively practiced. This concentration will be influenced by pH, which can be modeled by the same means. Given that the method is applied to a cell culture supernatant, an IgG antibody may not require the addition of salt or modification of pH to avoid significant losses. IgM antibodies may require the addition of salt, even to conductivity values approaching 30 mS/cm (about 2 times higher than physiological). In some embodiments involving the use of undissolved ureides and electropositive organic additives, IgG applications may be conducted at lower than physiological conductivity, potentially including values of 1 mS/cm or less, in which case substantial amounts of host proteins may be removed in conjunction with dissociating aggregates. Such applications may require that the concentration of the alkyl cations be increased to compensate for the amount that is lost through binding to host proteins. Lower operating conductivities in such circumstances may also enhance removal of DNA, endotoxin, and virus. In some embodiments, the disclosed methods will generally support antibody recovery greater than 95%, and usually 98-99%. Conductivity and pH conditions of the sample should typically be established before adding either the ureide or the alkyl cations.

In some embodiments, one effective means of evaluating conditions for clarified cell culture supernatants containing IgG monoclonal antibodies is to cover a range of 0.01 to 0.1% alkyl cations, and conductivities ranging from half-physiological to 2 times physiological. The ranges can be extended further if results indicate it may be helpful to do so, or narrowed and evaluated at finer increments.

In some embodiments, a convenient starting point for developing a purification procedure according to the disclosed methods for clarified cell culture supernatants is to use 0.025% cetyl trimethyl ammonium bromide.

In some embodiments, it may be advantageous to begin by dispersing an organic modulator in the protein preparation before adding the electropositive organic additive, since that practice may improve antibody recovery. Long incubation before addition of the electropositive organic additive appears to be unnecessary; 15 minutes or less is adequate, although there appears to be no disadvantage to longer incubation. Experimental data generally indicate that addition of allantoin in a supersaturating amount of about 1% increases the recovery of IgG.

In some embodiments, it is recommended that the alkyl cations cation be dissolved, for example in water or buffer, prior to its addition to the sample, to facilitate their rapid distribution throughout the protein preparation. Care should be taken to avoid persistent local excesses, for example by gradually infusing the dissolved alkyl cations into a well-mixing suspension. Incubation time should be at least 15 minutes, preferably 30, but appears not to benefit significantly from durations greater than 60 minutes.

The method may generally be practiced at ambient temperature but may be conducted at higher or lower temperatures, for example ranging from 4° to 37° C. Experimental data indicate that the temperature does not substantially alter the obtained results, which will leave the stability requirements of the protein the decisive factor in selection of operating temperature.

In some embodiments, the alkyl cation is dissolved or dispersed, for example in water or buffer, and the pH adjusted prior to its addition to the sample. This is because certain preparations of alkyl cations, such as free-base forms, are alkaline and have the potential to substantially alter the experimental conditions in an unintended manner.

In some embodiments involving the use of both super-staturated ureides and alkyl cations, it may generally be advantageous to begin by dispersing the ureide in the protein preparation before adding the alkyl cations, since experience with the ureide allantoin indicates that this practice can improve antibody recovery. Long incubation before addition of the electropositive organic additive appears to be unnecessary; 15 minutes or less is adequate, although there appears to be no disadvantage to longer incubation.

Multiple options exist for monitoring the aggregate dissociation ore removal achieved by the method, whether during method development or manufacturing. The simplest is to conduct analytical size exclusion chromatography on a column with suitable selectivity and monitor at a UV wavelength of 280 nm. This may reveal HMW (high molecular weight) aggregates, since they usually embody hydrodynamic dimension that reasonably conform to multiples of the size of the non-aggregated product. Heteroaggregates are commonly overlooked by this method since their hydrodynamic dimensions may be only modestly greater than those of the non-aggregated product. In such cases, the heteromorphic composition of the aggregate may be revealed by calculating the ratio of UV absorbance at 254 nm to absorbance at 280 nm, then comparing that value against the absorbance ratio for purified protein that is believed to be totally free of associated contaminants. Hetero-aggregates containing DNA, for example, will be revealed by an elevated ratio of 254/280.

In some embodiments, the disclosed methods can be integrated with treatment to remove the alkyl cations and potentially other components of the sample prior to subsequent purification. Such treatments may include exposure of the sample to solids bearing chemical moieties that are complementary in their nature to the characteristics of the alkyl cations with the goal that they sequester the alkyl cations from the remainder of the sample. Since alkyl cations are understood to be positively charged and hydrophobic, it follows that negatively charged surfaces, including hydrophobic negatively charged surfaces, should be especially useful for sequestering excess alkyl cations. Solids of other surface composition may be included to sequester other components of the sample.

In some embodiments, the disclosed methods can be integrated with one or more purification methods, including but not limited to protein A and other forms of biological affinity chromatography, anion exchange chromatography, cation exchange chromatography, hydrophobic interaction chromatography, immobilized metal affinity chromatography, hydroxyapatite or other mixed mode chromatography, and/or non-chromatographic methods such as precipitation and liquid-liquid extraction. It is within the purview of a person of ordinary skill in the art to develop appropriate conditions for the various methods and integrate them with the disclosed methods herein to achieve the necessary purification of a particular antibody.

EXAMPLES

Example 1

Independent effects of cetyl trimethyl ammonium bromide (CTAB) versus ethacridine. Cell culture harvest containing an IgG1 monoclonal antibody at a concentration of about 2 g/L was clarified by centrifugation and microfiltration. Aggregate content was 21.2% and host cell protein (HCP) content was 225,906 parts per million (ppm) of IgG. In a control series of experiments, different aliquots of clarified harvest were mixed with 0.01%, 0.02%, and 0.05% ethacridine and incubated stirring for 2 hours. In another series, CTAB was added to separate aliquots at the same concentrations. Solids were removed by centrifugation. CTAB reduced aggregates to 2.5-2.6%. Ethacridine reduced aggregates to 1.8-2.0%. However, where ethacridine was consistently observed to convert a subpopulation of light chain to apparent light chain dimer, CTAB did not.

Example 2

CTAB mixed with allantoin, followed by contact with functionalized solids. Cell culture harvest containing an IgG 1 monoclonal antibody at a concentration of about 2 g/L was clarified by centrifugation and microfiltration. Aggregate content was 10.5% and host protein content was 277,980 ppm of IgG. Allantoin was added in an amount of 1% w/v. CTAB bromide was added in an amount of 0.05% and the mixture incubated for 2 hours. Aggregates were reduced to 2.5% and host proteins were reduced to 156,002 ppm. Positively charged particles (Bio Works TREN high) were added in an amount of 5% v/v and incubated mixing for 4 hours. Solids were removed by centrifugation and microfiltration. Aggregates were reduced to 1.2% and host protein was reduced to 127,959 ppm, with an IgG recovery of 92%.

Example 3

In an example parallel to Example 2, and using the same source material, but where 0.05% CTAB was substituted by 0.05% methylene blue, aggregates were reduced to 5.4% versus the 2.5% by CTAB and host proteins were reduced to 223,612 ppm versus the 156,002 ppm by CTAB. After contact with the TREN particles, aggregates were reduced to 1.2% and host proteins to 94,780 by methylene blue.

Example 4

In an example parallel to Examples 2 and 3, and using the same source material, but where 0.05% CTAB was substituted by 0.025% ethacridine, aggregate was reduced to 3.5% and host protein to 174,210 ppm versus 2.5% and 156,002 by CTAB. After contact with TREN particles, aggregates were reduced to 1.2% and host proteins to 93,424 ppm by ethacridine, versus 1.2% and 127,959 by CTAB.

Example 5

In an example using the same source material as examples 2-4, but where 0.01% CTAB was combined with 0.04% methylene blue, aggregates were reduced to 3.4% and host protein to 157,483 versus CTAB alone with 2.5% aggregates and 156,002 ppm. After contact with TREN particles, the combination reduced aggregates to 1.3% and host proteins to 88,923 ppm, versus 0.05% CTAB alone with aggregates at 1.2% and HCP of 93,424 ppm.

Example 6

In an example using the same source material as examples 2-5, but where 0.01% CTAB was combined with 0.025% ethacrdine, aggregates were reduced to 3.2% and host protein to 155,788 versus CTAB alone with 2.5% aggregates and 156,002 ppm. After contact with TREN particles, the combination reduced aggregates to 1.2% and host proteins to 81,669 ppm, versus 0.05% CTAB alone with aggregates at 1.2% and HCP of 93,424 ppm.

Example 7

In an example beginning with the post-TREN treated material as produced by 0.05% CTAB as described in example 2, the sample was then passed through a pair of depth filters (PB1 and PC1, Sartorius). Aggregates were reduced to 0.2%, and host proteins were reduced to 31,987 ppm.

It will be understood by the person of ordinary skill in the art how to scale up or scale down the results from experiments such as those described in the above examples, to whatever volume required to meet their particular requirements.

All references cited herein are incorporated by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, chromatography conditions, and so forth used in the specification and claims are to be understood as being modified in all instances by the term "about." Accordingly, unless indicated to the contrary, the numerical parameters set forth in the specification and attached claims are approximations that may vary depending upon the desired performance sought to be obtained by the present disclosed methods.

Many modifications and variations of this disclosed methods can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the disclosed methods being indicated by the following claims.

The invention claimed is:

1. A method of reducing aggregate content in a preparation comprising an antibody, the method comprising: (a) contacting the preparation with an alkyl cation to form a mixture, wherein the alkyl cation is selected from a bromide or a chloride salt of a quaternary ammonium cation selected from the group consisting of cetrimonium (N,N,N-Trimethyl-1-hexadecanammonium), N,N,N-Trimethyl-1-heptadecanammonium, N,N,N-Trimethyl-1-octadecanammonium, N,N,N-Trimethyl-1-pentadecanammonium, and N,N,N-Trimethyl-1-tetradecanammonium; and (b) contacting the mixture with at least one functionalized solid to remove excess alkyl cation, wherein the functionalized solid comprises tris(2-ethylaminoethyl)amine (TREN), thereby providing a solution comprising the antibody and having a reduced aggregate content compared to the preparation prior to (a).

2. The method of claim 1, further comprising contacting the mixture with an aryl cation.

3. The method of claim 2, wherein the aryl cation is ethacridine or methylene blue.

4. The method of claim 1, wherein the alkyl cation comprises a bromide or a chloride salt of cetrimonium (N,N,N-Trimethyl-1-hexadecanammonium).

5. The method of claim 1, wherein the alkyl cation is present in a concentration range selected from the group consisting of: (a) from about 0.001% to about 1%; (b) from about 0.01 to about 1%, and (c) from about 0.02 to about 0.03% (weight/volume).

6. The method of claim 1, wherein an operating conductivity of the mixture is within a range selected from the group consisting of: (a) from about 0.1 to about 50 mS/cm; (b) from about 1 to about 30 mS/cm; and (c) from about 5 to about 15 mS/cm.

7. The method of claim 1, wherein an operating pH of the mixture is in a range selected from the group consisting of: (a) from about 4 to about 10; (b) from about 5 to about 9; and from about 6 to about 8.

8. The method of claim 1, wherein the mixture further comprises an antiviral agent that is not the alkyl cation, the antiviral agent being selected from the group consisting of chlorhexidine, benzalkonium chloride, methylene blue, ethacridine, and tri(n-butyl)phosphate.

9. The method of claim 1, wherein a surface of the at least one functionalized solid promotes a chemical interaction selected from the group consisting of: electrostatic interactions, hydrophobic interactions, hydrogen bonding, and metal affinity.

10. The method of claim 1, wherein the at least one functionalized solid is particulate.

11. The method of claim 1, wherein the antibody is a recombinant protein.

12. The method of claim 1, wherein the protein preparation is one selected from the group consisting of a cell-containing cell culture harvest, a substantially cell-free cell culture harvest, and a partially purified protein.

13. A method of reducing the aggregate content in a preparation comprising a soluble antibody, the method comprising:
  (a) contacting the preparation with an alkyl cation and allantoin to form a mixture, wherein the alkyl cation is present at a concentration from about 0.001% to about 0.1% (weight/volume), wherein the alkyl cation is selected from a bromide or a chloride salt of a quaternary ammonium cation selected from the group consisting of cetrimonium (N,N,N-Trimethyl-1-hexadecanammonium), N,N,N-Trimethyl-1-heptadecanammonium, N,N,N-Trimethyl-1-octadecanammonium, N,N,N-Trimethyl-1-pentadecanammonium, and N,N,N-Trimethyl-1-tetradecanammonium; and
  (b) removing solids from the mixture, thereby providing a soluble antibody having a reduced aggregate content compared to the preparation prior to (a).

14. The method of claim 13, wherein the antibody is an antibody of a class selected from IgG, IgA, IgE, IgD and IgM.

15. The method of claim 13, further comprising contacting the mixture with a functionalized solid comprising tris(2-ethylaminoethyl)amine (TREN).

16. The method of claim 13, wherein the allantoin is at a concentration between about 0.6% and 2% (weight/volume).

17. The method of claim 13, wherein the alkyl cation is a bromide or a chloride salt of cetrimonium (N,N,N-Trimethyl-1-hexadecanammonium).

* * * * *